US006160020A

United States Patent [19]
Ohannesian et al.

[11] Patent Number: 6,160,020
[45] Date of Patent: Dec. 12, 2000

[54] ALKALI METAL AND ALKALINE-EARTH METAL SALTS OF ACETAMINOPHEN

[75] Inventors: Lena A. Ohannesian, Blue Bell; David Nadig, Lansdale; John D. Higgins, III, West Chester, all of Pa.; Max Rey, Wallisellen, Sweden; Stephen A. Martellucci, Mont Clare, Pa.

[73] Assignee: McNeill-PPC, Inc., Fort Washington, Pa.

[21] Appl. No.: 09/100,284

[22] Filed: Jun. 19, 1998

Related U.S. Application Data

[63] Continuation-in-part of application No. 08/987,210, Dec. 9, 1997, abandoned, which is a continuation-in-part of application No. 08/771,176, Dec. 20, 1996, abandoned.

[51] Int. Cl.$^7$ .......................... A61K 31/16; C07C 233/00
[52] U.S. Cl. ........................................... 514/629; 564/215
[58] Field of Search .............................. 564/215; 514/629

[56] References Cited

U.S. PATENT DOCUMENTS

| | | | |
|---|---|---|---|
| 2,680,097 | 6/1954 | Stewart | 252/42.7 |
| 2,852,540 | 9/1958 | Young et al. | 260/404 |
| 2,998,450 | 8/1961 | Wilbert et al. | 260/562 |
| 3,431,293 | 3/1969 | Robertson et al. | 260/474 |
| 3,862,226 | 1/1975 | Harfenist | 260/562 |
| 3,956,490 | 5/1976 | Higuchi et al. | 424/233 |
| 3,987,170 | 10/1976 | Rohrbach et al. | 424/250 |
| 4,552,899 | 11/1985 | Sunshine et al. | 514/568 |
| 4,619,934 | 10/1986 | Sunshine et al. | 514/277 |
| 4,681,897 | 7/1987 | Brand | 514/557 |
| 4,783,465 | 11/1988 | Sunshine et al. | 514/255 |
| 4,812,446 | 3/1989 | Brand | 514/165 |
| 5,273,759 | 12/1993 | Simmons | 424/465 |
| 5,360,615 | 11/1994 | Yu et al. | 424/455 |
| 5,538,959 | 7/1996 | Mauskop | 514/165 |
| 5,914,129 | 6/1999 | Mauskop | 424/464 |

FOREIGN PATENT DOCUMENTS

| | | |
|---|---|---|
| 2417494 | 9/1979 | France . |
| 172949 | 1/1994 | India . |
| 629209 | 11/1976 | U.S.S.R. . |
| 1803833 A1 | 3/1998 | U.S.S.R. . |
| 1 428 803 | 3/1976 | United Kingdom . |
| 1 514 225 | 6/1978 | United Kingdom . |

OTHER PUBLICATIONS

Merck Index, 10th ed., 1983 p. 43.
Chemical Abstract 92:135418, 1980.
Chemical Abstract 125: 142293w, 1996.
Chemical Abstract 83: 193681t, vol. 83, 1975, p. 506.
Chemical Abstract 120: 182137b, vol. 120, 1994, p. 1354.
I.M. Kovach, Diss. Abstr., Int. B. 1975, 36 (2), 734–5.
Derwent Abstract 72,53946T (1972).
Chemical Abstracts, 88:74233S No. 11, (1978).
Getz, et al. J. Org. Chem. 1992, vol. 57, No. 6, pp. 1702–1706,"Mechanism of Hydrolysis of Benzamidomethyl Derivatives of Phenols and . . . ".
Derwent Abstract 74–25854V (1974).

*Primary Examiner*—Rebecca Cook
*Attorney, Agent, or Firm*—Bernard F. Plantz

[57] ABSTRACT

Isolated salts of acetaminophen are disclosed. Alkali metal and alkaline-earth metal salts of acetaminophen were formed by reacting the free acid of acetaminophen with the corresponding metal hydroxide and then immediately isolating the resulting salt. These salts have been found to be more water soluble and less bitter in taste than the free acid form of acetaminophen. The isolated salts may also be combined with other active ingredients.

64 Claims, 2 Drawing Sheets

ALKALI METAL AND ALKALINE-EARTH METAL SALTS OF ACETAMINOPHEN

This is a continuation-in-part of application Ser. No. 08/987,210, filed Dec. 9, 1997, abandoned which is a continuation-in-part of application Ser. No. 08/771,176, filed Dec. 20, 1996, abandoned both of which are hereby incorporated by reference.

FIELD OF THE INVENTION

The present invention relates to salts of acetaminophen and, more particularly, to alkali metal and alkaline-earth metal salts of acetaminophen.

BACKGROUND OF THE INVENTION

Acetaminophen (APAP) is a well established therapeutic agent having both analgesic and antipyretic activity. Acetaminophen's relatively poor solubility in water and its bitter taste, however, make it difficult to formulate into to consumer acceptable oral dosage forms. Most commercially available acetaminophen oral dosage forms incorporate a taste masking coating on the acetaminophen particles or employ flavors and sweeteners to mask the bitter taste of the drug.

Other approaches for dealing with the solubility and taste of acetaminophen include the formation of amino acid esters of acetaminophen. I. M. Kovach in *Diss. Abstr. Int. B* 1975, 36(2), 734–5 describes the synthesis of p-acetamidophenyl glycinate (APG), α-p-acetamidophenyl aspartate (AAPA) and β-p-acetamidophenyl aspartate (BAPA). These esters are reported to have a less bitter taste than acetaminophen. APG-HBr was five times more water soluble than acetaminophen, whereas BAPA-HCl was four times less water soluble than APAP.

It is also known that the formation of an appropriate salt of a hydrophobic compound, such as a lipophilic carboxylic acid, will usually improve the aqueous solubility of the compound. Sodium ibuprofen and sodium naproxen are examples of pharmaceutically active lipophilic carboxylic acids which have improved aqueous solubility in their salt form. These salts are typically formed by reacting the carboxylic acid with a strong base, such as sodium hydroxide or potassium hydroxide.

USSR Inventor's Certificate No. 629,209, published Sep. 11, 1978, describes a method of preparing bis-[β-(4-acetylaminophenyloxy)ethyl]ether by reacting 4-acetylaminophenol with an alkaline agent, such as potassium hydroxide, in a solution of an organic solvent, such as dimethylformamide, followed by reacting the resulting solution of potassium phenolate with chlorex at the boiling point of the reaction mixture. The resulting ether is reported as being useful for the treatment of animals with helminthic diseases.

USSR Inventor's Certificate 1,803,833, published Mar 23, 1993, describes a method of preparing acetaminophen for fluorescence intensity measurements. The acetaminophen sample was prepared by first dissolving in isopropyl alcohol and then treating with an 8% solution of potassium hydroxide solution and chloroform at a KOH:chloroform volume ratio of 3–4. Heating was then carried out for 15–20 minutes at 70–80° C. before the measurement of the sample's fluorescence intensity.

While both of the of the above-identified USSR Inventor's Certificates report the treatment of acetaminophen with potassium hydroxide, neither document reports the isolation of any potassium salt of acetaminophen.

M. S. Yu et al. in U.S. Pat. No. 5,360,615 discusses a pharmaceutical carrier system for enhancing the solubility of acidic, basic or amphoteric pharmaceuticals by partial ionization to produce a highly concentrated primarily non-aqueous solution suitable for filling softgels or for two-piece encapsulation or tablet formation. The acetaminophen solution comprised 25–40% (wt.) of acetaminophen, 0.4–1.0 moles of hydroxide ion per mole of acetaminophen and 1–20% (wt.) water in polyethylene glycol. An exemplary concentrated solution of acetaminophen suitable for use as a softgel fill contained 1 equivalent APAP (35% by wt.), 1 equivalent potassium hydroxide, and the balance polyethylene glycol 600.

U.S. Pat. No. 5,273,759 to D. L. Simmons describes the addition of $Mg(OH)_2$ in solid form to tablets containing APAP.

Both Yu et al. and Simmons fail to report the isolation of any discrete salts of acetaminophen.

A need exists for isolated salts of acetaminophen with improved aqueous solubility and taste when compared to the conventional form of acetaminophen.

SUMMARY OF THE INVENTION

The present invention provides isolated salts of acetaminophen. The isolated salts are preferably the alkali metal and alkaline-earth metal salts of acetaminophen.

In a further aspect of the invention the isolated salts have the formula:

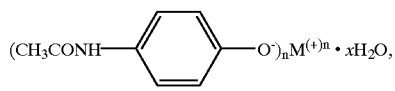

wherein n is 1 or 2, M is alkali metal when n is 1 and M is alkaline-earth metal when n is 2 and x is from 0 to about 10. These salts have been shown to have both improved aqueous solubility and a less bitter taste than the free acid form of acetaminophen. The invention also includes methods of making such salts.

The present invention also provides compositions comprising the isolated salts of acetaminophen and at least one other active ingredient selected from the group consisting of analgesics, decongestants, expectorants, antitussives, antihistamines, diuretics, gastrointestinal agents, diuretics, bronchodilators, sleep-inducing agents, and mixtures thereof.

Another aspect of the invention relates to the method of administering such salts, alone or in combination with other active ingredients, to mammals in the need of an analgesic and/or antipyretic therapeutic agent. The present invention further relates to orally adminsterable dosage forms containing salts of acetaminophen, alone or in combination with such other active ingredients.

DETAILED DESCRIPTION OF PREFERRED EMBODIMENTS

Figure 1:
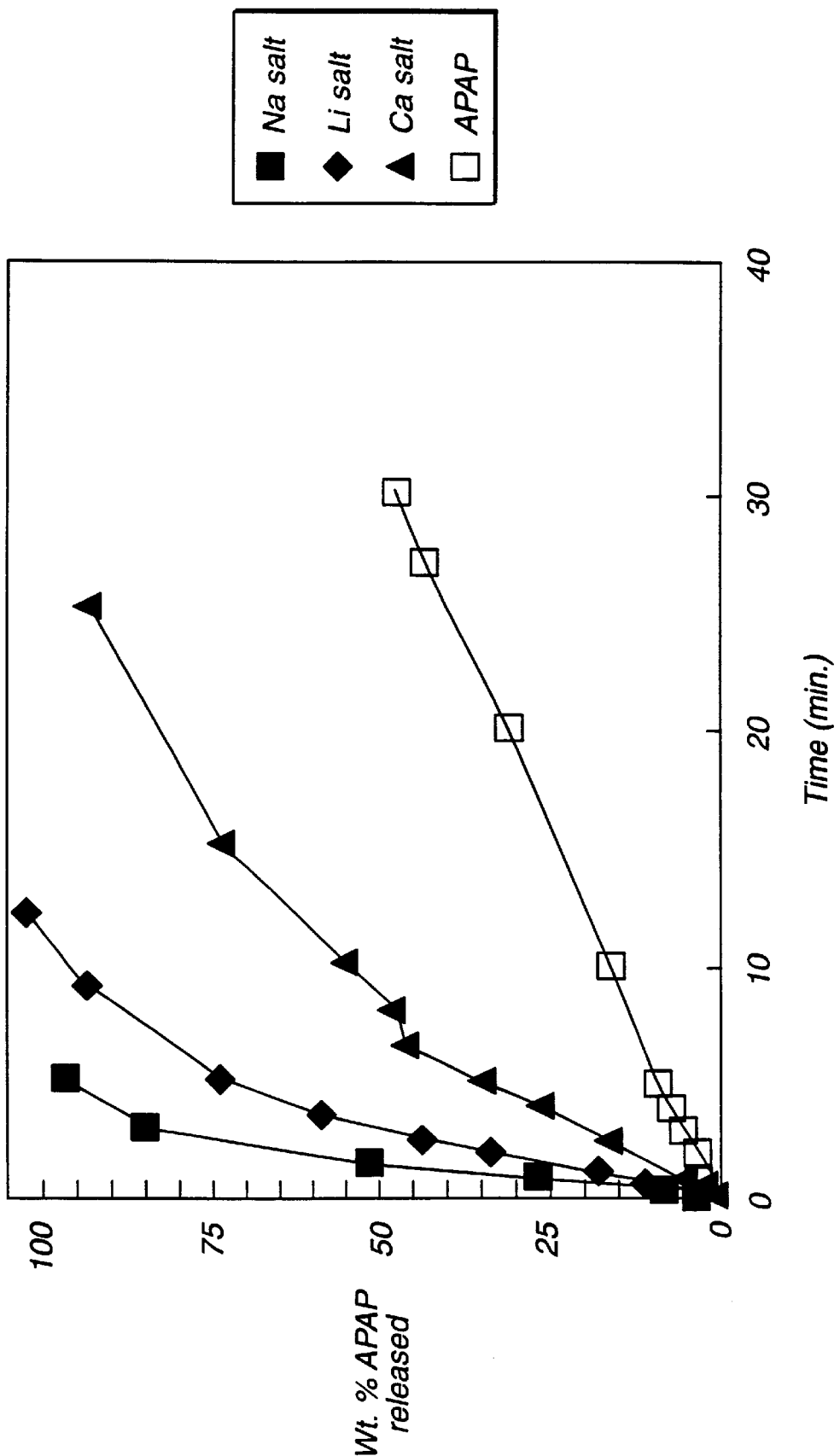
FIG. 1 is a plot the results of dissolution tests for tablets containing acetaminophen free acid and the isolated salts of acetaminophen.

Prior to the present invention there has been no reported isolation of any discreet salts (phenolates) of APAP.

Furthermore, in situ solution characterization of any deprotonated APAP species has not been reported either. As used in the present invention, the "free acid" of acetaminophen means the protonated phenolic form of APAP.

The lack of discussion on APAP salts in the scientific literature may be due in part to the fact that the anionic form of APAP is stable in aqueous solution (pH>11) for only a short period of time (<24 h). If the salt is not quickly isolated after formation, p-aminophenolate (PAP) can form and result in discoloration of the resulting product.

As used in the present invention, isolated salts of acetaminophen refers to salts of p-hydroxyacetanilide which are formed by the deprotonation of the phenolic proton of acetaminophen. The isolated salts are preferably the alkali metal and alkaline-earth metal salts of acetaminophen. In a further aspect of the invention the isolated salts have the formula:

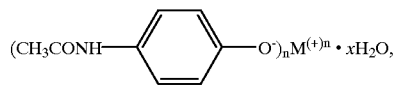

wherein n is 1 or 2, M is alkali metal when n is 1 and M is alkaline-earth metal when n is 2 and x is from 0 to about 10.

The salts of APAP are prepared via a one step aqueous reaction of APAP with the desired mono or divalent metal hydroxide. Suitable mono or divalent metal hydroxides include sodium hydroxide, calcium hydroxide, lithium hydroxide, potassium hydroxide, magnesium hydroxide and cesium hydroxide. The molar ratio of hydroxide to acetaminophen is about 1:2 to about 10:1, preferably about 1:2 to about 1:1. The APAP and metal hydroxide are dissolved in water or a mixture of water and a water-miscible organic solvent, such as acetonitrile, methanol, isopropanol, ethanol or tetrahydrofuran. The crude reaction products are then recovered or isolated by precipitation upon the addition of a less polar water miscible solvent such as acetonitrile, ethanol or tetrahydrofuran. Alternatively, the crude product can be recovered or crystallized by cooling (0° C.) or lyophilization of the reaction mixture. The recovery or isolation should generally be carried out as soon as the reaction product is formed so as to reduce the likelihood of product discoloration due to the formation of PAP. The final product may be dried under vacuum.

The APAP salts of the present invention are also amenable to cation exchange reactions. For example, an aqueous slurry or solution of a monovalent metal salt of acetaminophen is contacted with a divalent metal cation whereby the anhydrous, divalent metal salt of acetaminophen is formed via a cation exchange reaction. The salt is then immediately recovered. Specifically, $C_{16}H_{16}N_2O_4Ca$ may be prepared by reacting an aqueous solution of $C_8H_8NO_2Na$ with 0.5 equivalent of calcium chloride ($CaCl_2$). After drying, the resulting $C_{16}H_{16}N_2O_4Ca$ was found to be anhydrous.

In addition to the anhydrous form, various hydration states of APAP salts can be prepared depending on the reaction conditions. These hydrated salts preferably have less than 10 moles of water per mole of APAP salt, and includes, for example, acetaminophen sodium pentahydrate, acetaminophen sodium hexahydrate, acetaminophen sodium heptahydrate, acetaminophen calcium dehydrate and acetaminophen lithium hexahydrate.

The aqueous solubility at 22° C. of the APAP salts of the present invention is 490–540, 450–470 and 13 mg/mL for sodium, lithium and calcium, respectively. Accordingly, the sodium, lithium and calcium salts have solubilities equivalent to approximately 260–280, 250–270, and 10 mg/mL, respectively, of APAP free acid.

The APAP salts have significantly increased dissolution rates compared to the conventional free acid form of acetaminophen. In 0.1N hydrochloric acid using USP Dissolution Apparatus 2 (paddle speed: 50 rpm) at 37° C., the concentration of acetaminophen at 30 seconds was as follows:

| APAP Form (Powder) | Mg/mL of APAP |
|---|---|
| Sodium Salt | 0.30 |
| Lithium Salt | 0.32 |
| Calcium Salt | 0.20 |
| Free Acid (control) | 0.02 |

FIG. 1 illustrates the tablet dissolution rates of the salts of the present invention. The sodium, lithium and calcium salts of APAP and the conventional form of APAP were each compressed into tablets and the dissolution rates were evaluated using the conditions described above. The dissolution media was assayed for acetaminophen in the free acid form. FIG. 1 shows that the salts of the present invention have significantly higher acetaminophen dissolution rates that the conventional free acid.

The calcium and sodium salts of acetaminophen have been observed not to have the bitter properties of the conventional free acid form of acetaminophen. The calcium salt was almost tasteless, while the sodium salt was observed to be somewhat salty. The improved taste properties of the salts of the present invention will allow for acetaminophen oral dosage forms with improved taste to be formulated.

The onset of action of acetaminophen is believed to be hastened, relative to the free acid form, with the isolated salts of the present invention. The increase solubility of the salts of the present invention, results in faster peak acetaminophen plasma concentration. This property will potentially provide faster onset of action of the analgesic and/or antipyretic activity of acetaminophen.

The acetaminophen salts of the present invention may be administered to a mammal in a therapeutically effective amount, which is an amount that produces the desired therapeutic response upon oral administration, and can be readily determined by one skilled in the art. In determining such amounts, the particular compound being administered, the bioavailability characteristics of the compound, the dose regime, the age and weight of the patient, and other factors must be considered. A typical unit dose orally administered to a human would range from about 80–1000 mg (APAP free acid basis).

The compositions and methods of the present invention may also preferably include at least one other active ingredient selected from the group consisting of analgesics, decongestants, expectorants, antitussives, antihistamines, gastrointestinal agents, diuretics, bronchodilators, sleep-inducing agents and mixtures thereof. When the other active ingredient is selected from the group consisting of decongestants, expectorants, antitussives, antihistamines and mixtures thereof, the compositions are particularly useful for the treatment of cough, cold, cold-like and/or flu symptoms in mammals, such as humans. As used in the present invention, cold-like symptoms include coryza, nasal congestion, upper respiratory infections, allergic rhinitis, otitis, and sinusitis.

The analgesics useful in combination with the acetaminophen salts of this invention include acetyl salicylic acid, indomethacin, optically active isomers or racemates of ibuprofen, naproxen, flurbiprofen, carprofen, tiaprofenic acid, cicloprofen, ketoprofen, ketorolac, etodolac, indomethacin, sulindac, fenoprofen, diclofenac, piroxicam, benzydomine, nabumetone, tramadol, codeine, oxycodone, hydrocodone, pharmaceutically acceptable salts thereof and mixtures thereof. Cyclooxygenase-2 (COX-2) inhibitors, such as flosulide, nimesulide, celecoxib, 5-(4-aminosulfonyl-3-fluorophenyl)4-cyclohexyl-2-methyloxazole, meloxicam, nabumetone, etodolac, pharmaceutically acceptable salts thereof and mixtures thereof, may be used as an analgesic in the present invention.

The decongestants (sympathomimetics) suitable for use in the compositions of the present invention include pseudoephedrine, phenylpropanolamine, phenylephrine, ephedrine, pharmaceutically acceptable salts thereof and mixtures thereof.

The expectorants (also known as mucolytic agents) preferred for use in the present invention include guaifenesin, glyceryl guaiacolate, terpin hydrate, ammonium chloride, N acetylcysteine, bromhexine, ambroxol, domiodol, 3-iodo-1, 2-propanediol, pharmaceutically acceptable salts thereof and mixtures thereof.

The antitussives preferred for use in the present invention include those such as dextromethorphan, chlophedianol, carbetapentane, caramiphen, noscapine, diphenhydramine, codeine, hydrocodone, hydromorphone, fominoben, benzonatate, pharmaceutically acceptable salts thereof and mixtures thereof.

The antihistamines which may be employed include chlorpheniramine, brompheniramine, dexchlorpheniramne, dexbrompheniramine, triprolidine, doxylamine, tripelennamine, cyproheptadine, hydroxtzine, pyrilamine, azatadine, promethazine, acrivastine, astemizole, cetirizine, ketotffen, loratidine, temelastine, terfenadine, norastemizole, fexofenadine, pharmaceutically acceptable salts thereof and mixtures thereof.

Examples of gastrointestinal agents preferred for use in the present invention include anticholinergics, including: atropine, clidinium and dicyclomine; antacids, including: aluminum hydroxide, bismuth subsalicylate, bismuth subcitrate, calcium carbonate and magaldrate; anti-gas agents, including simethicone; H2-receptor antagonists, including: cimetidine, famotidine, nizatidine and ranitidine; laxatives, including: phenolphthalein and casanthrol; gastroprotectants, including: sucralfate and sucralfate humid gel; gastrokinetic agents, including: metoclopramide and eisaprode; proton pump inhibitors, including omeprazole and antidiarrheals, including: diphenoxylate and loperamide; pharmaceutically acceptable salts thereof and mixtures thereof.

The diuretics useful in the invention include caffeine and pamabrom. Also useful are bronchodilators such as terbutaline, aminophylline, pinephrine, isoprenaline, metaproterenol, bitoterol, theophylline, albuterol, pharmaceutically acceptable salts thereof and mixtures thereof.

Sleep-inducing agents suitable for use in the invention include melatonin, estazolam, zolpidem, promethacine, pharmaceutically acceptable salts thereof and mixtures thereof.

The term "pharmaceutically acceptable salts" refers to salts prepared from pharmaceutically acceptable non-toxic bases including inorganic bases and organic bases. Salts derived from nonorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like.

As with the acetaminophen salts of the present invention, these other active ingredients are administered to a mammal in a therapeutically effective amount, which is an amount that produces the desired therapeutic response upon oral administration, and can be readily determined by one skilled in the art. In determining such amounts, the particular compound being administered, the bioavailability characteristics of the compound, the dose regime, the age and weight of the patient, and other factors must be considered. Many of these other active ingredients, as well as their acceptable dosage ranges are described in the following: U.S. Pat. No. 4,552,899 to Sunshine et al., issued Nov. 12, 1985; U.S. Pat. No. 4,783,465 to Sunshine et al., issued Nov. 8, 1988; and U.S. Pat. No. 4,619,934 to Sunshine et al., issued Oct. 28, 1986, which are all incorporated by reference herein. Other antitussives, expectorants, antihistamines, decongestants, and gastrointestinal agents suitable for use in the invention are described in *Remington's Pharmaceutical Sciences*, Mack Publishing Co., Easton, Pa., 18$^{th}$ ed. Chapters 39, 42, 43, 58 and 59 (1990), which is hereby incorporated by reference. These other active ingredients may be administered concomitantly as a combination product with the acetaminophen salt or they may be administered as separate products prior to or after the administration of the APAP salt.

The acetaminophen salts of the present invention, alone or in combination with the other active ingredients, are generally administered orally in a solid dosage form. Suitable solid preparations include as swallowable, chewable or fast dissolving tablets, pills, capsules, caplets, powders, wafers, sachets, gelatin coated tablets, softgels and granules. In preparing solid dosage forms, the salt of acetaminophen, alone in combination with such other active ingredients, can be mixed with conventional solid fillers or carriers, such as corn starch, talc, calcium phosphate, calcium sulphate, calcium stearate, magnesium stearate, stearic acid, sorbitol, microcrystalline cellulose, mannitol, gelatin, natural or synthetic gums, such as carboxymetbylcellulose, methylcellulose, alginate, dextran, acacia gum, karaya gum, locust bean gum and other conventional carriers. Additionally, other excipients such as diluents, binders, lubricants, disintegrants, colors and flavoring agents may be employed. The dosage form can also be film coated. It may also be desirable to coat the acetaminophen salt and/or other active ingredients with a conventional, pharmaceutically acceptable polymeric film prior to the preparation of the dosage form.

Conventional methods can be used for preparing the solid dosage forms of the present invention. Suitable techniques are described in *Remington's Pharmaceutical Sciences,* 18th Ed., Chapter 89 (1990) which is hereby incorporated by reference.

The following example illustrates a specific embodiment of the present invention. This invention, however, is not confined to the specific limitations set forth in this example but rather to the scope of the appended claims. Unless otherwise stated, the percentages and ratios given below are by weight.

EXAMPLE I

This Example discloses the preparation of acetaminophen sodium ($C_8H_8NO_2Na.6H_2O$).

30 mL 1N NaOH solution (0.030 mol) were added to a stirred suspension of 4.53 g (0.033 mol) acetaminophen in 25 mL water. After all solids dissolved, 200 mL acetonitrile was added while the solution was rapidly stirred. The resulting white precipitate (9.15 g, 99% yield as the 6-hydrate) was collected on a frit, washed with tetrahydrofuran (THF) and dried at room temperature. $^1$H NMR (DMF d$_7$) δ9.4 (s, 1H, NH), 7.1 (m, 2H, Ar—H), 6.3 (m, 2H, Ar—H),1.96 (s, 3H, CO—CH$_3$); IR (cm$^{-1}$, KBr) 3421 (broad, OH), 1635 (sharp, CO), 1594 (sharp), 1534 (sharp), 1500 (sharp), 1279 (sharp); Combustion analysis calculated for $C_8H_8NO_2Na.6H_2O$: C 34.16, H 7.12, N 4.98; found C 34.05, H 6.96, N 5.00; Water content calculated for $C_8H_8NO_2Na.6H_2O$: 38%, Found: 38% (Karl Fischer); FAB mass spectral analysis m/e calculated for $C_8H_8NO_2Na.6H_2O$: 173, found 174 (M+1). The aqueous solubility at 22° C. was 493 mg/mL.

EXAMPLE II

This Example discloses the preparation of acetaminophen sodium ($C_8H_8NO_2Na.7H_2O$).

80 g (2.00 mol) NaOH was dissolved in 400 mL water and added dropwise to a flask charged with 302 g (2.00 mol) APAP dissolved in 2100 mL i-propanol, at 50° C. with stirring. The solution was cooled to room temperature, whereupon an off-white precipitate formed. The solids were filtered, washed with three 200 mL portions of i-propanol, and dried under a vacuum (500 g, 84% as the 7-hydrate). The $^1$H NMR and IR spectra were identical to that of $C_8H_8NO_2Na.6H_2O$. Combustion analysis calculated for $C_8H_8NO_2Na.7H_2O$: C 32.11 H 7.41 N 4.68; Found: C 31.99, H 7.38, N 4.31; Water content calculated for $C_8H_8NO_2Na.7H_2O$: 42.1%; Found 42.7% (Karl Fischer). The aqueous solubility at 22° C. was 541 mg/mL.

EXAMPLE III

This Example discloses the preparation of acetaminophen calcium ($C_{16}H_{16}N_2O_4Ca.2H_2O$).

5 g (0.033 mol) APAP and 1.22 g (0.016 mol) Ca(OH)$_2$ were suspended in 200 mL water and the mixture was stirred for 4 h, whereupon all solids went into solution. The solution was frozen in a bath of liquid nitrogen and lyophilized, leaving a light microcrystalline off-white solid (5.44 g, 100% crude yield based on the hydrate X 2). $_1$H NMR (DMF d$_7$) δ9.39 (s, 2H, NH), 7.15 (m, 4H, Ar), 6.80 (m, 4H, Ar), 2.10 (s, 6H, CO—CH$_3$). IR 3287 (broad), 1648 (sharp, C=O), 1594, 1541, 1500, 1279 (sharp) Combustion analysis calculated for $C_{16}H_{16}N_2O_4Ca.2H_2O$: C 51.05, H 5.36, N 7.45; 9.6, Found: C 51.21, H 5.21, N 7.63. Water content calculated (Karl Fischer) for $C_{16}H_{16}N_2O_4Ca.2H_2O$: 9.6%, Found: 9.8%. The aqueous solubility at 22° C. was 13 mg/mL.

EXAMPLE IV

This Example discloses the preparation of acetaminophen lithium ($C_8H_8NO_2Li.6H_2O$).

5 g (0.033 mol) APAP was dissolved in 30 mL i-propanol/THF (1:3, degassed with argon). This solution was added rapidly to a flask charged with 1.38 g of (0.033 mol) LiOH.H$_2$O dissolved in 20 mL water (argon degassed). The colorless solution was stored at 0° C. for 16 h, whereupon white crystals formed. The crystals were filtered under argon, washed with THF and dried under a vacuum for 16 h (4.25 g, 6 hydrate). $^1$H NMR (DMF-d$^7$) δ9.39 (s, 1H, NH), 7.15 (m, 2H, Ar—H), 6.80 (m, 2H, Ar—H), 2.10 (s, 3H, CO—CH$_3$); IR 3568 (sharp), 3402, 3243 (broad), 1672, 1618 (sharp), 1533, 1501, 1407, 1267, 1174 (sharp). Combustion analysis calculated for $C_8H_8NO_2Li.6H_2O$: C 36.23, H 7.60, N 5.28; Found: C 36.67, H 7.68, N 5.23; Water content calculated (Karl Fischer) for $C_8H_8NO_2Li.6H_2O$: 40.1%, Found: 38.4%. The aqueous solubility at 22° C. was 455 mg/mL.

EXAMPLE V

This Example discloses an alternative preparation of acetaminophen lithium ($C_8H_8NO_2Li.6H_2O$).

Acetaminophen (15.1 g; 0.1 mol), water, 90 mL and lithium hydroxide 1 N (100 mL, 0.1 mol) were placed in a 2 L beaker. After the solution became clear, acetonitrile (1500 mL) was added. The resulting white solids were filtered, washed with THF (ca. 500 mL) and dried at ambient leaving a dry white solid (23.0 g, 87% based on $C_8H_8NO_2Li.6H_2O$). $^1$H NMR (DMF-d$^7$) δ2.0 (s,3H, CO—CH3), 6.5 (m, 2H, Ar—H), 7.2 (m, 2H, Ar—H), 9.3 (s,1H, Ac—NH—Ar); IR 3568 (sharp), 3402, 3243 (broad), 1672, 1618 (sharp), 1533, 1501, 1407, 1267, 1174 (sharp). Combustion analysis calculated for $C_8H_8NO_2Li.6H_2O$: C 36.23, H 7.60, N 5.28; Found: C 36.56, H 7.56, N 5.05. Water content calculated (Karl Fischer) for $C_8H_8NO_2Li.6H_2O$: 40.1%, Found: 40.0%. The aqueous solubility at 22° C. was 472 mg/mL.

EXAMPLE VI

This Example discloses the preparation of an anhydrous acetaminophen calcium ($C_{16}H_{16}N_2O_4Ca$).

Acetaminophen (90.6 g, 0.60 mol) was suspended in 135 mL water and a solution containing sodium hydroxide (24.0 g, 0.6 mol) and 36 mL water was added at 18–26° C. over 30 min. To the resulting NaAPAP-slurry, a solution containing calcium chloride (CaCl$_2$) (44.1 g, 0.3 mol) and 54 mL water was added at 20–25° C. over 30 min. at room temperature. The reaction mixture was then heated to 60° C. within 60 min. Immediately after reaching 60° C., the slurry was cooled to 20° C. within 60 min. and stirred at 20° C. for 30 min. The resulting $C_{16}H_{16}N_2O_4Ca$ (79 g, 78%) was filtered off, washed with i-propyl alcohol (75 mL) and dried overnight at 80° C. under vacuum. $^1$H NMR (D$_2$O) δ7.01 (d,8,4H), 6.57 (d,8,4H), 2.06 (s, 6H, CO—CH$_3$). IR (cm$^{-1}$): 1651 (sharp, C=O), 1506, 1276, 854 (sharp). Combustion analysis calculated for $C_{16}H_{16}N_2O_4Ca$: C 55.65, H 4.7, N 8.23; Found: C 55.80, H 4.53, N 8.13.

EXAMPLE VII

A study was conducted in dogs to determine the bioavailability of acetaminophen sodium. The free acid form of acetaminophen was used as the control. Compressed cylindrical pellets having the following composition were prepared:

Acetaminophen Sodium—compressed neat (no excipients). Control—150 mg APAP, 30 mg microcrystalline cellulose, and 30 mg dextrates.

Eight male purebred beagles having a body weight at initial dosing of approximately 9 to 14 kg were used in the study. The dogs were fed PMI® Certified Canine Diet Meal No. 5007 and water, both ab libitum. The dogs were fasted overnight for approximately 12 hours prior to dosing and food was returned 4 hours after dosing.

The dogs were divided into two groups and each group was dosed with either acetaminophen sodium or the control (free acid APAP) pellets. A single dose equivalent to 300 mg of acetaminophen free acid was administered via an oral gavage using a stomach tube. Each dose was followed by 20 mL of water. After a period of one week, the each group was dosed again, but with the other form of acetaminophen. Twelve blood samples were collected form each dog on each dosing day (1 prior to dosing and 11 thereafter). The plasma was separated and tested for acetaminophen.

The following summarizes the pharmacokinetic measurements for acetaminophen:

| Parameter | APAP Sodium | Control |
|---|---|---|
| AUC (ug-hr/mL) | 31.4 ± 5.7 | 27.4 ± 6.1 |
| $C_{max}$ (ug/mL) | 23.6 ± 4.2 | 19.4 ± 6.9 |
| $T_{max}$ (hr) | 0.27 ± 0.1 | 0.60 ± 0.3 |

AUC = areas under the plasma concentration-time curve to the last quantifiable concentration.
$C_{max}$ = peak plasma concentration.
$T_{max}$ = peak time.

Figure 2:
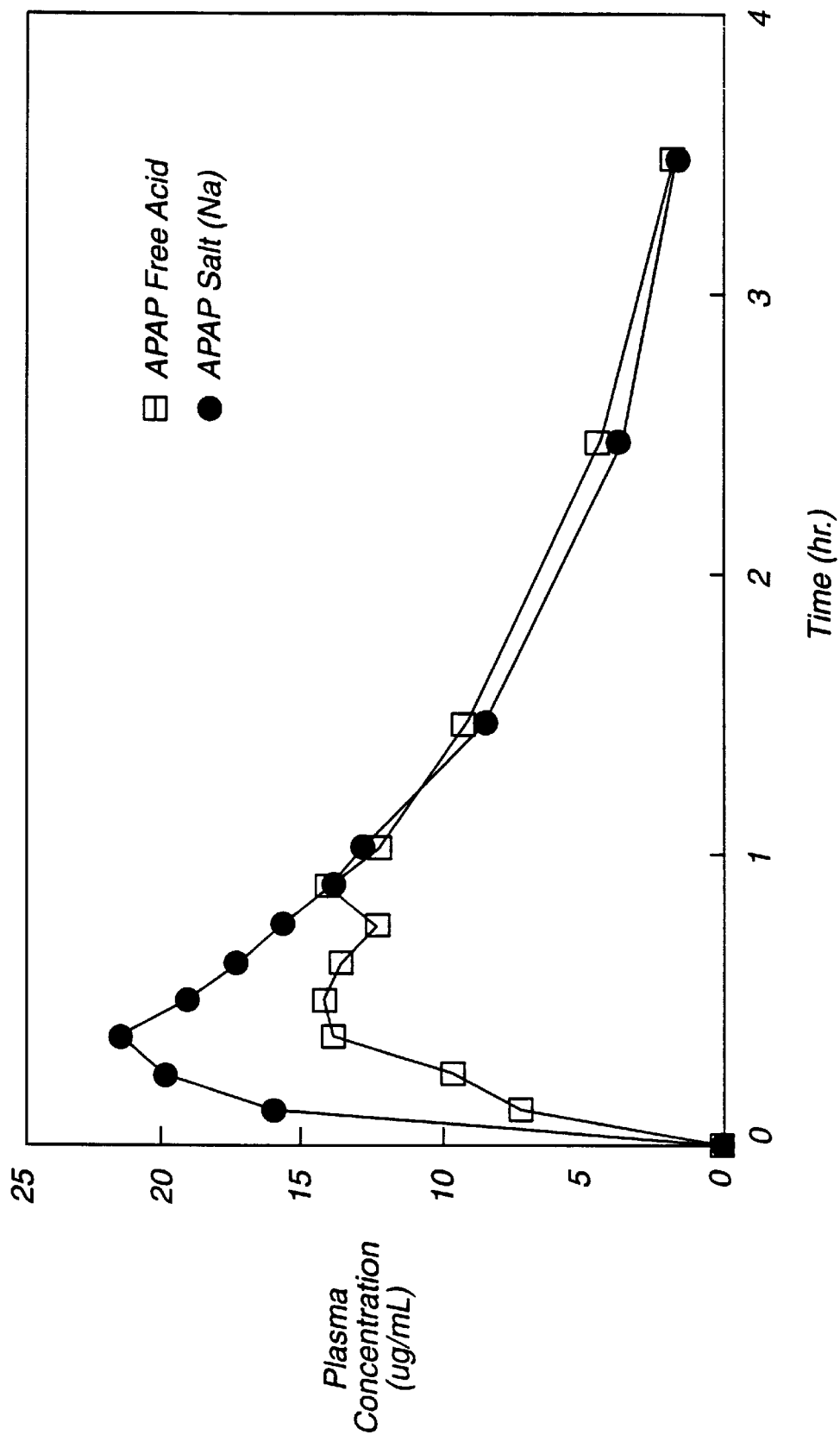
FIG. 2 is a plot of acetaminophen plasma concentrations versus time for the bioequivelency study in dogs described in Example VII.

FIG. 2 is a plot of the acetaminophen plasma concentration-time curve. This Figure demonstrates that the acetaminophen salt of the present invention is absorbed faster than the free acid acetaminophen control. The faster $T_{max}$ for the acetaminophen salt suggests faster onset of action of the analgesic and antipyretic activities relative to the free acid control.

EXAMPLE VIII

This Example discloses the preparation and testing of tablets containing anhydrous calcium acetaminophen (CaAPAP) and one other active ingredient selected from the group of chlorpheniramine maleate (CPM), dextromethorphan hydrobromide (DEX), diphenhydramine hydrochloride (DPH) and pseudoephedrine hydrochloride (PE). The target weight of the tablet (free APAP basis) was 325 mg. The following ingredients were used to make the tablets:

| Ingredient | Formulation 1 (mg/Tab) | Formulation 2 (mg/Tab) | Formulation 3 (mg/Tab) | Formulation 4 (mg/Tab) |
|---|---|---|---|---|
| CaAPAP | 368.23 | 368.23 | 368.23 | 368.23 |
| CPM | 2.00 | — | — | — |
| DEX | — | 15.00 | — | — |
| DPH | — | — | 25.00 | — |
| PE | — | — | — | 30.00 |
| Microcrystalline Cellulose (Avicel PH 200) | 520.77 | 507.77 | 497.77 | 492.77 |
| $SiO_2$ (Cab-O-Sil M5) | 4.50 | 4.50 | 4.50 | 4.50 |
| Mg Stearate NF | 4.50 | 4.50 | 4.50 | 4.50 |

Appropriate amounts of these ingredients were weighed to make a 180 g batch. After sieving, the ingredients were combined and mixed using a PK Blender. The ingredients were then tableted using a single-punch Korsh tablet press. The weight, hardness, thickness and disintegration times were evaluated and are reported below. The dissolution of the CaAPAP was measured using USP Method II apparatus by monitoring the APAP concentration in gastric fluid(GF). The percent dissolution of APAP from the tablet formulations at 2 min. is also reported.

| | Formulation 1 | Formulation 2 | Formulation 3 | Formulation 4 |
|---|---|---|---|---|
| Weight Range (mg) | 917 ± 6 | 900 ± 4 | 907 ± 9 | 913 ± 4 |
| Thickness range (mm) | 5.72 ± 0.02 | 5.65 ± 0.03 | 5.72 ± 0.02 | 5.56 ± 0.02 |
| Hardness range (kP) | 7.9 ± 0.1 | 9.1 ± 0.3 | 7.1 ± 1.1 | 8.8 ± 0.5 |
| Disintegration time (sec) | 10 to 15 | 10 to 15 | 20 | 15 to 20 |
| % dissolution of CaAPAP at 2 minutes in GF | 100% | — | 100% | 100% |

Various modifications can be made from the above-described embodiments without departing from the spirit and scope of the present invention.

What is claimed is:

1. An isolated alkali metal or alkaline-earth metal salt of acetaminophen.

2. The salt of claim 1 wherein the alkali metal is selected from the group consisting of lithium, sodium, potassium and cesium.

3. The salt of claim 1 wherein the alkaline-earth metal is selected from the group consisting of calcium and magnesium.

4. The salt of claim 1 in a hydrated form.

5. The salt of claim 1 in an anhydrous form.

6. The salt of claim 5 wherein the alkaline-earth metal is calcium.

7. A solid orally adminsterable dosage form comprising a therapeutically effective amount of the salt of claim 1.

8. A method of treating a mammal in need of an analgesic or antipyretic agent, comprising the oral administration of a therapeutically effective amount of an isolated alkali metal or alkaline-earth metal salt of acetaminophen.

9. The method of claim 8 wherein the alkali metal is selected from the group consisting of lithium, sodium, cesium and potassium.

10. The method of claim 8 wherein the alkaline-earth metal is selected from the group consisting of calcium and magnesium.

11. The method of claim 8 wherein the salt is in a hydrated form.

12. The method of claim 8 wherein the salt is in an anhydrous form.

13. The method of claim 12 where in the alkaline-earth metal is calcium.

14. A method of eliciting an analgesic or antipyretic response in a mammal, comprising the oral administration of a therapeutically effective amount of an isolated alkali metal or alkaline-earth metal salt of acetaminophen.

15. The method of claim 14 wherein the alkali metal is selected from the group consisting of lithium, sodium, cesium and potassium.

16. The method of claim 14 wherein the alkaline-earth metal is selected from the group consisting of calcium and magnesium.

17. The method of claim 14 wherein the salt is in a hydrated form.

18. The method of claim 14 wherein the salt is in an anhydrous form.

19. The method of claim 18 wherein the alkaline-earth metal is calcium.

20. The isolated compound:

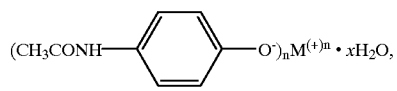

wherein n is 1 or 2, M is alkali metal when n is 1 and M is alkaline-earth metal when n is 2 and x is from 0 to about 10.

21. The compound of claim 20 wherein the alkali metal is selected from the group consisting of sodium potassium, cesium and lithium.

22. The compound of claim 20 wherein the alkaline-earth metal is selected from the group consisting of calcium and magnesium.

23. The compound of claim 20 in a hydrated form.

24. The compound of claim 20 in an anhydrous form.

25. The compound of claim 24 wherein the alkaline-earth metal is calcium.

26. A method of preparing an isolated alkali metal or alkaline-earth metal salt of acetaminophen, comprising:

reacting acetaminophen with an alkali metal or alkaline-earth metal metal hydroxide in the presence of a solvent to form a reaction mixture and immediately recovering the resulting salt from the reaction mixture.

27. The method of claim 26 wherein the solvent is water or a water-miscible organic liquid.

28. The method of claim 26 wherein the salt is recovered by crystallization with a water-miscible solvent.

29. The method of claim 26 wherein the salt is recovered by lyophilization.

30. A method of preparing an anhydrous, isolated salt of acetaminophen, comprising:

contacting a monovalent metal salt of acetaminophen with a divalent metal cation whereby a divalent metal salt of acetaminophen is formed via a cation exchange reaction and immediately recovering the resulting anhydrous, divalent metal salt of acetaminophen.

31. The method of claim 30 wherein an aqueous solution or slurry of said monovalent metal salt of acetaminophen is contacted with said divalent metal cation and the resulting anhydrous salt is recovered by vacuum drying.

32. The method of claim 30 wherein the anhydrous salt is $C_{16}H_{16}N_2O_4Ca$.

33. The method of claim 32 wherein said anhydrous salt is formed by a cation exchange reaction between acetaminophen sodium and calcium chloride.

34. A composition comprising an isolated alkali metal or alkaline-earth metal salt of acetaminophen and at least one other active ingredient selected from the group consisting of analgesics, decongestants, expectorants, antitussives, antihistamines, gastrointestinal agents, diuretics, bronchodilators and, sleep-inducing agents or a mixture thereof.

35. The composition of claim 34 wherein the alkali metal is selected from the group consisting of lithium, sodium, potassium and cesium.

36. The composition of claim 34 wherein the alkaline-earth metal is selected from the group consisting of calcium and magnesium.

37. The composition of claim 34 wherein the salt is in a hydrated form.

38. The composition of claim 34 wherein the salt is in an anhydrous form.

39. The composition of claim 38 wherein the alkaline-earth metal is calcium.

40. The composition of claim 37 comprising a solid orally administerable dosage form.

41. A method of treating a mammal in need of an analgesic or antipyretic agent, comprising the oral administration of a therapeutically effective amount of the composition of claim 34.

42. The method of claim 41 wherein the alkali metal is selected from the group consisting of lithium, sodium, cesium and potassium.

43. The method of claim 42 wherein the alkaline-earth metal is selected from the group consisting of calcium and magnesium.

44. The method of claim 41 wherein the salt is in a hydrated form.

45. The method of claim 41 wherein the salt is in an anhydrous form.

46. A method of eliciting an analgesic or antipyretic response in a mammal, comprising the oral administration of a therapeutically effective amount of the composition of claim 34.

47. The method of claim 46 wherein the alkali metal is selected from the group consisting of lithium, sodium, cesium and potassium.

48. The method of claim 46 wherein the alkaline-earth metal is selected from the group consisting of calcium and magnesium.

49. The method of claim 46 wherein the salt is in a hydrated form.

50. The method of claim 46 wherein the salt is in an anhydrous form.

51. A pharmaceutical composition comprising the isolated compound

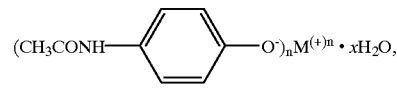

wherein n is 1 or 2, M is alkali metal when n is 1 and M is alkaline-earth metal when n is 2 and x is from 0 to about 10, and at least one other active ingredient selected from the group consisting of analgesics, decongestants, expectorants, antitussives, antihistamines, gastrointestinal agents, diuretics and bronchodilators or a mixture thereof.

52. The composition of claim 51 wherein the alkali metal is selected from the group consisting of sodium, potassium, cesium and lithium.

53. The composition of claim 51 wherein the alkaline-earth metal is selected from the group consisting of calcium and magnesium.

54. The composition of claim 51 wherein the isolated compound is in a hydrated form.

55. The composition of claim 51 wherein the isolated compound is in an anhydrous form.

56. The composition of claim 51 wherein the analgesic is selected from the group consisting of acetyl salicylic acid, indomethacin, an optically active isomer or racemate of ibuprofen, naproxen, flurbiprofen, carprofen, tiaprofenic acid, cicloprofen, ketoprofen, ketorolac, etodolac, indomethacin, sulindac, fenoprofen, diclofenac, piroxicam, benzydomine, nabumetone, tramadol, codeine, oxycodone, hydrocodone, flosulide, nimesulide, celecoxib, 5-(4-aminosulfonyl-3-fluorophenyl)-4-cyclohexyl-2-methyloxazole, meloxicam, nabumetone and etodolac; or a pharmaceutically acceptable salt thereof or a mixture thereof.

57. The composition of claim 51 wherein the decongestant is selected from the group consisting of pseudoephedrine, phenylpropanolamine, phenylephrine and ephedrine; or a pharmaceutically acceptable salt thereof or a mixture thereof.

58. The composition of claim 51 wherein the expectorant is selected from the group consisting of guaifenesin, glyceryl guaiacolate, terpin hydrate, ammonium chloride, N acetylcysteine and bromhexine, ambroxol, domiodol and 3-iodo-1,2-propanediol; or a pharmaceutically acceptable salt thereof and or a mixture thereof.

59. The composition of claim 51 wherein the antitussive is selected from the group consisting of dextromethorphan, chlophedianol, carbetapentane, caramiphen, noscapine, diphenhydramine, codeine, hydrocodone, hydromorphone, fominoben and benzonatate; or a pharmaceutically acceptable salt thereof or a mixture thereof.

60. The composition of claim 51 wherein the antihistamine is selected from the group consisting of chlorpheniramine, brompheniramine, dexchlorpheniramne, dexbrompheniramine, triprolidine, doxylamine, tripelennamine, cyproheptadine, hydroxtzine, pyrilamine, azatadine, promethazine, acrivastine, astemizole, cetirizine, ketotifen, loratidine, temelastine, terfenadine, norastemizole and fexofenadine; or a pharmaceutically acceptable salt thereof or a mixture thereof.

61. The composition of claim 51 wherein the gastrointestinal agent is selected from the group consisting of atropine, clidinium and dicyclomine, aluminum hydroxide, bismuth subsalicylate, bismuth subcitrate, simethicone, calcium carbonate, magaldrate, cimetidine, famotidine, nizatidine, ranitidine, phenolphthalein, casanthrol, sucralfate and sucralfate humid gel, metoclopramide, eisaprode, omeprazole, diphenoxylate and loperamide; or a pharmaceutically acceptable salt thereof or a mixture thereof.

62. The composition of claim 51 wherein the other active ingredient is a diuretic which is selected from the group consisting of caffeine and pamabrom.

63. The composition of claim 51 wherein the other active ingredient is a bronchodilator which is selected from the group consisting of terbutaline, aminophylline, pinephrine, isoprenaline, metaproterenol, bitoterol, theophylline and albuterol; or a pharmaceutically acceptable salt thereof or a mixture thereof.

64. The composition of claim 51 wherein the other active ingredient is a sleep-inducing agent which sleep-inducing agent is selected from the group consisting of melatonin, estazolam, zolpidem and promethacine; or a pharmaceutically acceptable salt thereof or a mixture thereof.

* * * * *